(12) United States Patent
Bazille

(10) Patent No.: US 9,737,338 B2
(45) Date of Patent: Aug. 22, 2017

(54) BOTTOM-LOADING POLYAXIAL BONE ANCHORING SYSTEM

(71) Applicant: SPINEVISION, Antony (FR)

(72) Inventor: Julien Bazille, Massy (FR)

(73) Assignee: SPINEVISION, Antony (FR)

( * ) Notice: Subject to any disclaimer, the term of this patent is extended or adjusted under 35 U.S.C. 154(b) by 0 days.

(21) Appl. No.: 14/888,459

(22) PCT Filed: May 2, 2014

(86) PCT No.: PCT/FR2014/051051
§ 371 (c)(1),
(2) Date: Mar. 8, 2016

(87) PCT Pub. No.: WO2014/177819
PCT Pub. Date: Nov. 6, 2014

(65) Prior Publication Data
US 2016/0183982 A1    Jun. 30, 2016

(30) Foreign Application Priority Data

May 2, 2013   (FR) .................................. 13 54053

(51) Int. Cl.
*A61B 17/70*      (2006.01)
*A61B 17/86*      (2006.01)

(52) U.S. Cl.
CPC ...... *A61B 17/7032* (2013.01); *A61B 17/7035* (2013.01); *A61B 17/7037* (2013.01); *A61B 17/8605* (2013.01)

(58) Field of Classification Search
CPC ......................................... A61B 17/70–17/746
USPC .................................................. 606/246–279
See application file for complete search history.

(56) References Cited

U.S. PATENT DOCUMENTS

| 7,947,065 | B2 | 5/2011 | Hammill, Sr. et al. |
| 2007/0135817 | A1 | 6/2007 | Ensign |
| 2008/0119006 | A1 | 5/2008 | Lee |
| 2012/0179212 | A1 | 7/2012 | Jackson et al. |

*Primary Examiner* — Nicholas Plionis
(74) *Attorney, Agent, or Firm* — Bachman & LaPointe, P.C.

(57) ABSTRACT

A polyaxial bone anchoring system comprises a bone anchoring member provided with a hemispherical head and a tubular barrel comprising a base traversed by an axial channel of which the cross-section is greater than the cross-section of the hemispherical head, the channel having, in the lower part, a frustoconical housing that widens in the direction opposite the hemispherical head and, upstream from the frustoconical housing, a transverse shoulder of which the inner cross-section is substantially equal to the cross-section of the hemispherical head, the system further comprising a conical split ring of which the outer surface matches the inner surface of the frustoconical housing and of which the minimum cross-section when idle is smaller than the nominal cross-section of the hemispherical head, said ring being made from a deformable material.

7 Claims, 3 Drawing Sheets

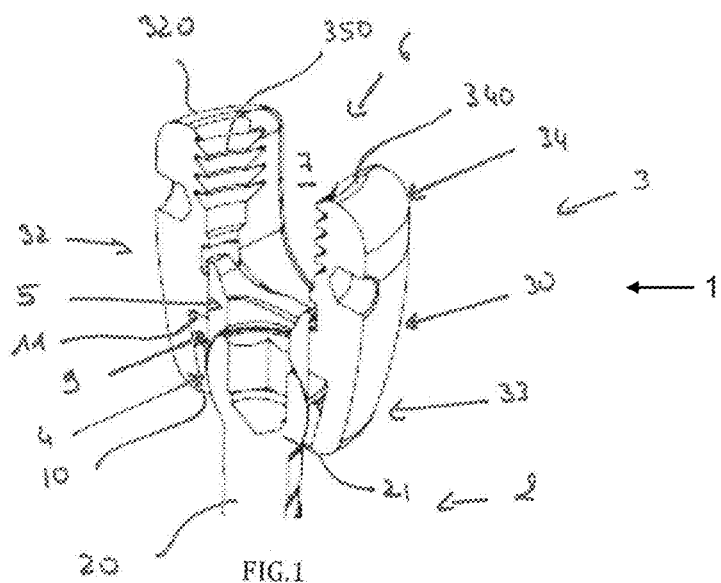
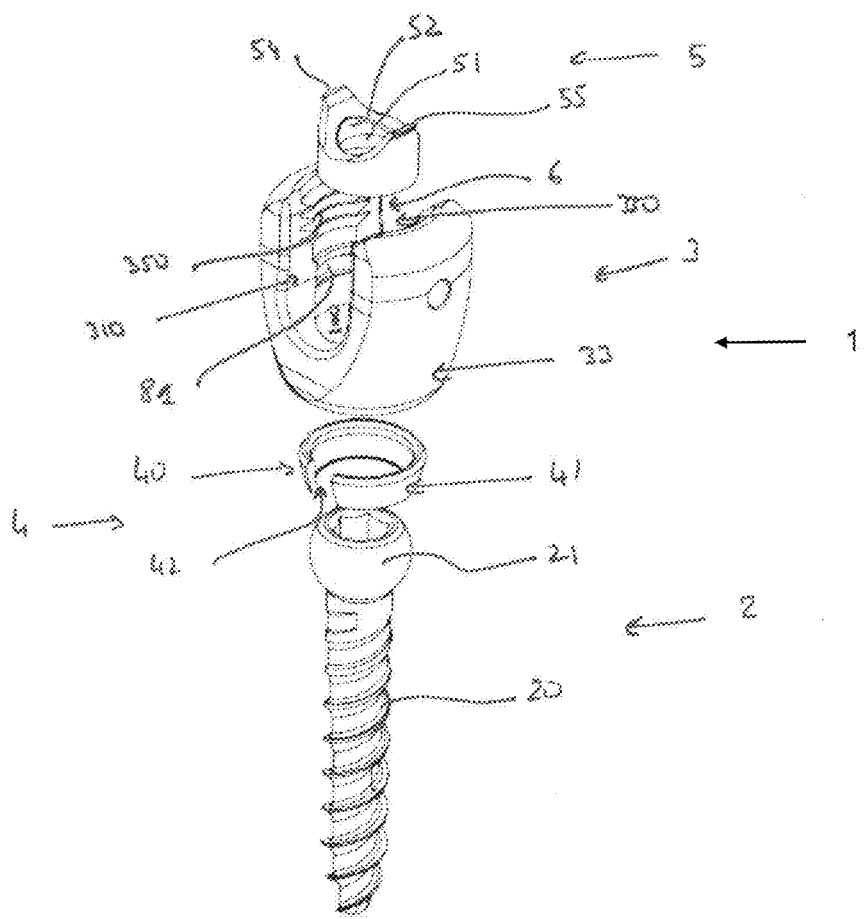
FIG.1
FIG.2

BOTTOM-LOADING POLYAXIAL BONE ANCHORING SYSTEM

BACKGROUND

The invention relates to a polyaxial bone anchoring system intended for correcting and stabilizing vertebrae of a spinal column.

The invention more particularly relates to a bottom-loading polyaxial bone anchoring system.

Conventionally, the vertebral anchoring systems comprise bone anchoring elements, such as screws, respectively comprising a threaded rod intended to be fixed in the pedicle of a vertebra and provided at one of its ends with a connector for coupling the bone anchor element with a stabilizing element, such as a connecting rod.

In complex assemblies comprising several spinal segments, bone anchoring systems hinged at the junction of the bone anchoring elements and the connectors are commonly used. This is called a polyaxial bone anchoring system or a polyaxial pedicle screw. Adjusting the position of the bone anchoring systems and thus facilitating the mounting of the connecting rods into the latter thus becomes possible.

In order to provide greater modularity as regards the type and the dimensions of the bone anchoring elements and the connectors to be assembled, bone anchoring systems enabling the bottom-loading of the bone anchoring elements with the connectors have been developed.

Among this type of bone anchoring system, the one described in patent U.S. Pat. No. 7,947,065 can be mentioned. The bone anchoring system described comprises a connecting assembly comprising a connector consisting of an upper connecting member and a lower connecting member, an upper retaining ring accommodated in the lower part of the upper connecting member and a split retaining ring accommodated in the lower connecting member of the connector. The lower surface of the upper connecting member has a plurality of ramps so arranged as to cooperate with the lower split ring when assembling the screw with the connector. These ramps make it possible to open the split ring so as to let the spherical head of the screw through the split ring. When the connection assembly is mounted on the screw head, the split ring is thus pushed by the screw head to come into contact with the upper retaining ring which compresses a spring to cause the contacting of the lower split ring with the ramps, thus causing opening of the split ring to allow the passage of the screw head through said ring. Once the screw head is gone therethrough, the spring drives the split ring to the lower part of the lower connecting member, thus preventing the screw head from going out of the connecting assembly.

The connecting system mentioned in patent U.S. Pat. No. 7,947,065, and more generally the bottom-loading bone anchoring systems of the prior art, has/have the disadvantage of being relatively complex. As a matter of fact, the implementation of several elements is required for the screw head to be inserted into and retained in the connector, such as a spring, two retaining means and a ramp system.

The invention aims at remedying these problems by providing a bone anchoring system enabling the bottom-loading of the bone anchoring element into a connector in a simple and fast way while providing a satisfactory behavior of the bone anchoring element in the connector.

SUMMARY

For this purpose, and according to a first aspect, the invention provides a polyaxial bone anchoring system comprising a bone anchoring element provided with a hemispherical head and a tubular barrel for coupling a stabilizing element with the bone anchoring element, with said tubular barrel comprising a base which an axial channel having a cross-section greater than the cross-section of the hemispherical head goes through, with said axial channel having, in its lower part, a frustoconical housing which widens in the direction opposite the hemispherical head and upstream from the frustoconical housing, a transverse shoulder having an inner cross-section substantially equal to the cross-section of the hemispherical head, with the polyaxial bone anchoring system further comprising a conical split ring having an outer surface matching the inner surface of the frustoconical housing and having a minimum cross-section, when idle, which is smaller than the nominal cross-section of the hemispherical head, with said ring being made of a material deformable between an expanded position allowing the passage of the hemispherical head through the split ring and a retracted position having a cross-section smaller than the minimum cross-section, when idle, for the insertion thereof into the frustoconical housing, with the frustoconical housing having a height greater than the height of the split ring and in the vicinity of the shoulder, a cross-section greater than the outer cross-section of the ring.

Because of this configuration and the dimensions of the base and of the ring, the assembly of the bone anchoring element and the coupling barrel is provided only by a joint motion of the split ring in the frustoconical housing and of the hemispherical head in the axial channel.

The frustoconical housing advantageously comprises a radial groove in the vicinity of the shoulder. This makes it possible to provide sufficient space to allow the expansion of the ring as it goes through the hemispherical head.

The axial channel of the base advantageously comprises a widened cross-section, in the vicinity of the shoulder. This makes it possible to facilitate the insertion of the hemispherical head into the axial channel.

The bone anchoring system advantageously comprises means for locking the bone anchoring element in the tubular barrel, with said locking means being positioned in the axial channel of the base, upstream from the frustoconical housing.

According to a particular configuration, the locking means comprises a cradle body having an upper surface so shaped as to accommodate the connecting rod and a lower surface so shaped as to accommodate the hemispherical head.

The axial channel of the base is advantageously so arranged with the locking means as to allow an axial motion of the locking means in the channel, between a position in which the tubular barrel is free to rotate on the hemispherical head of the bone anchoring element and a position in which the tubular barrel is locked on the hemispherical head.

The anchoring system advantageously comprises means for guiding the locking means between a position in which the tubular barrel is free to rotate on the hemispherical head of the bone anchoring element and a position in which the tubular barrel is locked on the hemispherical head. According to a particular embodiment, the locking means comprise a cradle body extended by two lugs which extend outwards and are intended to be respectively accommodated in a groove provided in the inner wall of the base, with said lugs and grooves forming the means for guiding the locking means.

According to a particular embodiment, the coupling barrel has two U-shaped side recesses to accommodate a connecting rod and a central axial channel allowing the engagement of a plug for locking the bone anchoring system, with the central axial channel opening into the axial channel of the base (33).

BRIEF DESCRIPTION OF THE FIGURES

Other objects and advantages of the invention will become apparent from the following description with reference to the appended drawings, wherein:

FIG. 1 shows a partial longitudinal sectional view of a bone anchoring system according to a first embodiment of the invention;

FIG. 2 shows an exploded view of the bone anchoring system of FIG. 1;

DETAILED DESCRIPTION

Figures 3A, 3B:
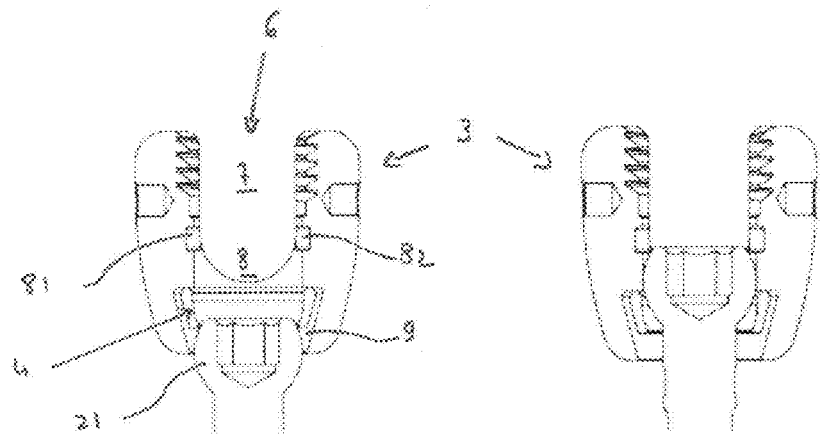
FIGS. 3a to 3e show the steps of assembling the components of the bone anchoring system of FIG. 1.

In relation to FIGS. 1 and 2, a bone anchoring system 1 according to a first embodiment is disclosed, which comprises a bone anchoring element 2 intended to be implanted in a vertebra, with a connector 3 having the shape of a tubular barrel (it will then be called a coupling barrel) as well as means 4 for retaining the bone anchoring element 2 in the connector 3 and means 5 for locking the bone anchoring element in the connector 3 in a given position.

The bone anchoring element 2 has a threaded pin 20 extended at one of its ends by a hemispherical head 21. The hemispherical head will be referred to, hereafter, as the "screw head 21".

The coupling barrel 3 comprises a bellmouth body 30 provided with two arms 32, 34 and a base 33.

The two arms are so arranged as to define two U-shaped side recesses 310, 330 for accommodating a connecting rod (not shown) as well as a first central axial channel 7 intended for accommodating means (not shown) for locking the bone anchoring system 1, of the caging nut type. For this purpose, the inner face of each of the arms 32, 34 has a screw thread 350 adapted to cooperate with the outer thread of the caging nut. The upper ends 320, 340 of the arms 30, 32 define an inlet opening 6 of the caging nut.

The base 33 is gone through by a central axial channel 8 hereinafter referred to as the second axial channel as opposed to the central axial channel of the upper part referred to as the first axial channel. The second channel 8, which opens into the first channel 7 has, at the lower end of the base 33, an inlet opening 10 to allow the passage of the screw head 21 into the tulip body 30. For reasons which will be explained later, the second channel 8 has a cross-section larger than the cross-section of the screw head 21.

The second channel 8 advantageously comprises, in its lower part 9, a housing having a frustoconical shape which widens in a direction opposite the screw head 21. As discussed below, the frustoconical housing 9 is intended for accommodating the retaining means (split ring), and the screw head 21.

Upstream from the frustoconical housing 9, i.e. away from the screw head 21 when the latter is mounted in the coupling barrel 3, the second channel 8 comprises a transverse shoulder 11 defining the upper portion of the truncated housing 9. The shoulder 11 advantageously has a specific cross-section for letting the screw head 21 through in the upper part of the second channel 8 while preventing the passage of the retaining means. In the embodiment described, the shoulder 11 is substantially equal to the cross-section of the screw head 21.

Hereafter, the portion of the tubular body 30 defined by the inner thread 350 of the arms 32, 34 characterizes the upper part of the coupling barrel 3 (or the tubular body 30). Similarly, the portion of the base 33 defined by the frustoconical housing 9 characterizes the lower part of the coupling barrel 3 (or the tubular body 30) while the portion of the base 33 which extends between the upper part and the lower part of the coupling barrel 3 characterizes the intermediate part of the coupling barrel 3.

As discussed below, the intermediate part is intended to accommodate the locking means or simply lock 5 of the screw head 21 in position relative to the coupling barrel 3 and, during the assembly of the bone anchoring element with the coupling barrel 3, the screw head 21, whereas the lower part is intended to accommodate the means for retaining the screw head 21 in the coupling barrel 3.

Figures 3C, 3D, 3E:
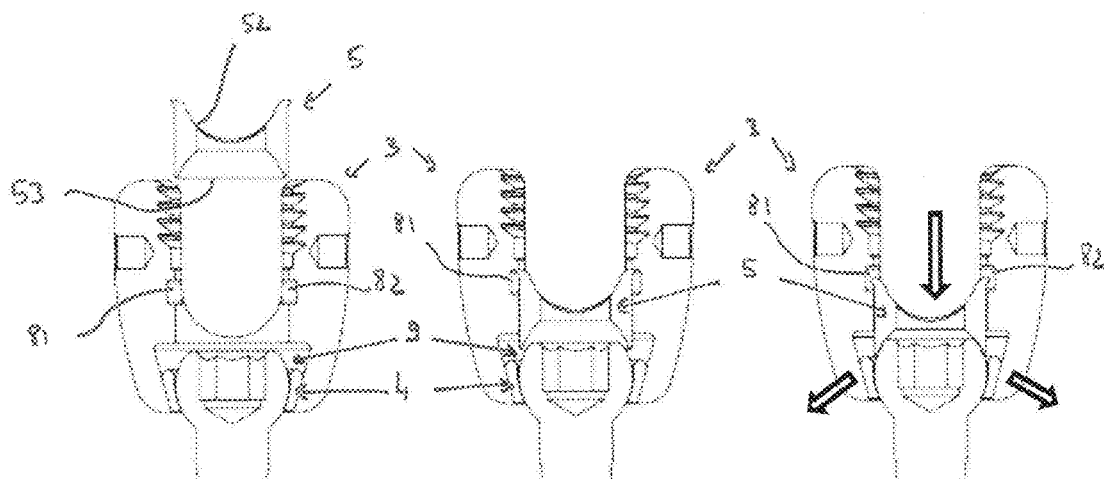

In the example shown, the intermediate portion comprises, in the upper part, in the extension of the arms 32, 34, two grooves 81, 82 formed in the inner wall of the base 33. The grooves 81, 82 make it possible to guide the locking means between a position in which the motion of the coupling barrel 3 on the screw head 21 is prevented and a position in which the motion of the coupling barrel 3 on the screw head 21 is prevented (locked position) as illustrated in FIGS. 3d and 3e and described below. Advantageously, the intermediate portion has an inlet with a widened cross-section (not shown) so as to facilitate the insertion of the screw head 21 therein.

According to the invention, the retaining means is shaped as a transversally split ring 4 formed to have an outer surface matching the inner surface of the frustoconical housing 9 of the lower part of the coupling barrel 3.

The split ring 4 is advantageously made of a deformable material. The material is so selected that the split ring 4 is deformable between an expanded position allowing the passage of the screw head 21 through said ring and a retracted position wherein the split ring 4 has a cross-section enabling the insertion thereof into the truncated housing 9. More specifically, the split ring 4 shall have, in the retracted position, a cross-section enabling the passage thereof through the lower inlet opening 10 of the coupling barrel 3. Besides, the split ring 4 is so shaped as to have, when idle, a minimum cross-section smaller than the nominal cross-section of the screw head 21.

The split ring 4 advantageously has a height smaller than the height of the frustoconical housing 9. This arrangement is advantageous in that, as discussed below, the motion of the split ring 4 inside the frustoconical housing 9, with the split ring 4 being movable between an upper position allowing the passage of the screw head through the split ring 4 and a lower position wherein the screw head is retained in the frustoconical housing 9, in the lower part of the coupling barrel.

The means 5 for locking the screw head 21 in the coupling barrel 3 consists of a cradle-forming part, hereinafter called the locking cradle 5, intended to be positioned between the screw head 21 and the connecting rod when the latter is positioned in the bone anchoring system 1. In the embodiment described, the locking cradle 5 comprises a cradle body 50 provided with an axial through bore 51 and has an upper contact surface 52 the shape of which matches that of the outer surface of the connecting rod and a lower contact surface 53 the shape of which matches that of the screw head 21.

The cradle body 50 has an outer diameter slightly smaller than that of the second axial channel 8.

The cradle body 50 is advantageously extended by two lugs 54, 55 which extend outwards, i.e. in a direction opposite the bore 51 of the cradle body. The lugs 54, 55 are intended to be accommodated respectively in one of the grooves 81, 82 arranged in the inner wall of the base 33. The lugs 54, 55 form, with the grooves 81, 82, means for guiding the locking cradle 5 between the position in which the coupling barrel 3 is free to rotate on the screw head 21 and the locking position in which the coupling barrel 3 is locked on the screw head 21.

The grooves 81, 82 advantageously have dimensions allowing some axial clearance for the locking cradle 5 when the latter is mounted in the intermediate portion. The cradle body 50 can thus be moved slightly upwards or downwards when mounted in the coupling barrel 3. As will be explained hereafter, such clearance allows the coupling cradle 5 to move from a position in which the coupling barrel 3 is free to rotate on the screw head 21 to a locked position in which the coupling barrel 3 is locked in position on the screw head 21, with any rotational movement being prevented.

Advantageously, the outer surface of the cradle body 50 intended for accommodating the connecting rod may have streaks, rough spots, ribs or the like in order to increase the frictional engagement between the cradle body 50, the connecting rod and the locking means when the latter is positioned in the first axial channel of the coupling barrel 3. Similarly, a rod having streaks, rough spots, ribs or the like can be provided to improve the frictional engagement between said elements.

The grooves 81, 82 and the cradle body 50 have dimensions so that, when the cradle body 50 is in the locking position, the cradle body 50 has a portion which extends into the frustoconical housing 9 so as to come into contact with the screw head 21.

The bone anchoring element 2 is assembled with the coupling barrel 3 as follows.

The first step consists in snapping the split ring 4 in the frustoconical housing 9. For this purpose, according to a snapping technique selected among others, the ring 4 is positioned relative to the coupling barrel 3 so that its slot 42 is placed opposite the lower inlet opening 10. A compressive force is then exerted onto the split ring 4 to have the two arms 40, 41 move closer to the split ring 4 and to position the split ring 4 in the retracted position allowing it to go through the opening 10. The ring 4 is then pushed into the frustoconical housing 9. Once partially inserted therein, the split ring 4 is subject to a tilting motion to be brought into the correct direction, i.e. so positioned as to have the widest portion opposite the lower inlet opening 10. Once positioned in the frustoconical housing 9, the split ring 4 returns to its shape when idle.

Once the split ring 4 is positioned in the frustoconical housing 9, the anchoring element is snapped into the coupling barrel 3. To do this, the screw head 21 is placed in front of the lower inlet opening 10 and inserted into the frustoconical housing 9. As the nominal cross-section of the screw head 21 is greater than the minimum inner cross-section of the ring when idle, the screw head 21 drives the split ring 4 towards the top of the frustoconical housing 9 until the latter comes into contact with the shoulder 11 (FIG. 3a). As the translational movement of the screw head 21 towards the inlet opening 6 of the caging nut goes on, the screw head 21 enters the second channel 8 intended for accommodating the coupling cradle 5. Because the ring is locked by the shoulder 11, the arms 40, 41 of the split ring 4, move away from one another because of the thrust force of the screw head 21, until they reach an expanded position allowing the passage of the screw head 21 through said split ring 4. Once the screw head 21 is in the second channel, the split ring 4 returns to its position when idle in the frustoconical housing 9 (FIG. 3b).

The bone anchoring system 2 is then pulled in the opposite direction, towards the inlet opening 10 of the screw head 21 so as to bring the screw head 21 back in the frustoconical housing 9. When moving, the screw head 21 drives the split ring 4, which is in the idle position, towards the lower inlet opening to reach the position in which the screw head 21 is held in the coupling barrel 3 as shown in FIG. 3c. It should be noted that, once assembled with the coupling barrel 3, the bone anchoring element 2 can no longer be removed without one of the items being broken.

The following step consists in snapping the coupling cradle 5 in the coupling barrel 3. To do this, the coupling cradle 5 is brought in front of the upper inlet opening 6 and is then slipped inside the coupling barrel 3 to be positioned in the second channel, in the intermediate portion of the coupling barrel 3 (FIGS. 3c and 3d).

As described above, the locking cradle can move axially in the second axial channel. When the coupling cradle 5 is placed in the upper position in the second central channel as illustrated in FIG. 3d, some clearance is left between the lower surface of the cradle and the screw head 21 so that the screw head 21 can rotate in the coupling barrel 3. When the cradle is placed in the lower position, the cradle is pressed against the screw head, thereby preventing the screw head 21 from moving in the coupling barrel 3, with the split ring 4 meanwhile exercising side forces preventing any expansion thereof. In other words, any motion of the screw head 21 is prevented by the ring and the cradle. FIG. 3 illustrates the stresses exerted between the elements to lock the multi-axiality of the screw head 21.

Thus, once the bone anchoring element 2 is assembled with the coupling barrel 3, the cradle is positioned.

Figure 4:
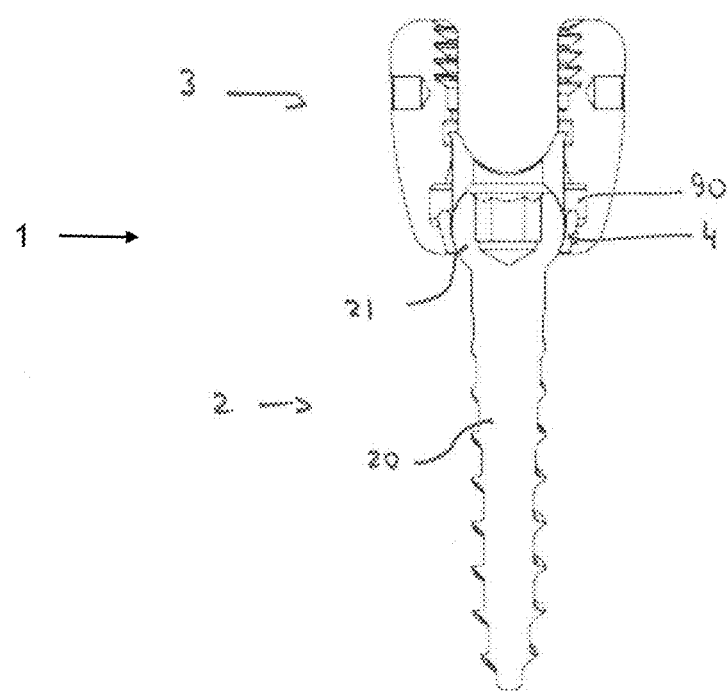
FIG. 4 shows a longitudinal sectional view of a bone anchoring system according to a second embodiment of the invention.

According to a particular configuration illustrated in FIG. 4, the lower part advantageously comprises a radially extending inner groove 90. The presence of such a groove allows greater expansion of the retaining means during the passage of the screw head 21. The positioning of the screw head 21 in the coupling barrel 3 is thereby facilitated, and this is also true for head screws having relatively large dimensions.

The invention is described above as an example. It should be understood that the persons skilled in the art may provide various alternative embodiments of the invention without departing from the scope of the invention.

The invention claimed is:
1. A polyaxial bone anchoring system comprising:
a bone anchoring element provided with a hemispherical head,
a tubular barrel for coupling a stabilizing element with the bone anchoring element, said tubular barrel comprising a tubular barrel body having a lower opening end and an opening upper end,
means for locking the bone anchoring element in the tubular barrel, said locking means being situated inside the tubular barrel body, and
a conical split ring,
said tubular barrel body comprising a base which an axial channel having a cross-section greater than a cross-section of the hemispherical head goes through, with said axial channel having a frustoconical housing which widens in the direction opposite to the lower opening end of the tubular barrel body, said tubular barrel body comprising a transverse shoulder having an inner cross-section substantially equal to the cross-section of the hemispherical head, said transverse shoulder delimiting with the lower opening end of the tubular barrel the frustoconical housing said conical split ring having an outer surface matching the inner surface of the frustoconical housing of the barrel body and having a minimum cross-section, when idle, which is smaller than the cross-section of the hemispherical head, with said ring being made of a material which is deformable between an expanded position allowing the passage of the hemispherical head through the split ring and a retracted position having a cross-section smaller than the minimum cross-section, when idle, for the insertion thereof into the frustoconical housing, with the frustoconical housing having a height greater than the height of the split ring and, around the shoulder, a cross-section greater than the outer cross-section of the ring, wherein said frustoconical housing comprises, a radial groove situated around the transverse shoulder.

2. The polyaxial bone anchoring system according to claim 1, wherein the axial channel of the base has a widened cross-section in the vicinity of the shoulder.

3. The polyaxial bone anchoring system according to claim 1, wherein the axial channel of the base is configured to allow an axial motion of the locking means in the channel between a position in which the tubular barrel is free to rotate on the hemispherical head of the bone anchoring element and a position in which the tubular barrel is locked on the hemispherical head.

4. The polyaxial bone anchoring system according to claim 1, further comprising means for guiding the locking means between a position in which the tubular barrel is free to rotate on the hemispherical head of the bone anchoring element and a position in which the tubular barrel is locked on the hemispherical head.

5. The polyaxial bone anchoring system according to claim 4, wherein the locking means comprise a cradle body extended by two lugs which extend outwardly and are configured to be respectively accommodated in a groove provided in the inner wall of the base, with said lugs and grooves forming the means for guiding the locking means.

6. The polyaxial bone anchoring system according to claim 1, wherein the locking means comprise a cradle body having an upper surface shaped for accommodating the stabilizing element and a lower surface shaped to accommodate the hemispherical head.

7. The polyaxial bone anchoring system according to claim 1, wherein the tubular barrel body has two U-shaped side recesses to accommodate a connecting rod and a central axial channel allowing the engagement of a plug for locking the bone anchoring system, with the central axial channel opening into the axial channel of the base.

* * * * *